US00PP30191P2

(12) United States Plant Patent
Pieters

(10) Patent No.: US PP30,191 P2
(45) Date of Patent: Feb. 12, 2019

(54) ***CHRYSANTHEMUM* PLANT NAMED 'GED17VIG8R'**

(50) Latin Name: ***Chrysanthemum* X *morifolium***
Varietal Denomination: GED17VIG8R

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 15/731,855

(22) Filed: Aug. 15, 2017

(51) Int. Cl.
*A01H 5/02* (2018.01)

(52) U.S. Cl.
USPC ..... Plt./287

(58) Field of Classification Search
USPC ..... Plt./263.1, 284, 286, 287
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'GED17VIG8R', characterized by its upright, outwardly spreading and uniformly rounded plant habit; vigorous growth habit; freely branching habit; dense and full plant habit; dark green-colored leaves; uniform and freely flowering habit; long flowering period; and relatively large decorative-type inflorescences with dark red purple-colored ray florets.

1 Drawing Sheet

Botanical designation: *Chrysanthemum* X *morifolium*.
Cultivar denomination: 'GED17VIG8R'.

BACKGROUND OF THE INVENTION

The present invention relates to a new and distinct cultivar of *Chrysanthemum* plant, botanically known as *Chrysanthemum* X *morifolium* and hereinafter referred to by the name 'GED17VIG8R'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant is a naturally-occurring whole plant mutation of *Chrysanthemum* X *morifolium* 'Vigorelli Violet', disclosed in U.S. Plant Pat. No. 23,965. The new *Chrysanthemum* plant was discovered and selected by the Inventor as a single plant from within a population of plants in a controlled greenhouse environment in Oostnieuwkerke, Belgium in October, 2015

Asexual reproduction of the new *Chrysanthemum* plant by vegetative terminal cuttings was first conducted in a controlled greenhouse environment in Oostnieuwkerke, Belgium in January, 2016. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'GED17VIG8R'. These characteristics in combination distinguish 'GED17VIG8R' as a new and distinct *Chrysanthemum* plant:

1. Upright, outwardly spreading and uniformly rounded plant habit; vigorous growth habit.
2. Freely branching habit; dense and full plant habit.
3. Dark green-colored leaves.
4. Uniform and freely flowering habit.
5. Long flowering period.
6. Relatively large decorative-type inflorescences with dark red purple-colored ray florets.

Plants of the new *Chrysanthemum* differ from the mutation parent, 'Vigorelli Violet', primarily in ray floret color as plants of 'Vigorelli Violet' have lighter red purple-colored ray florets.

Plants of the new *Chrysanthemum* can be compared to plants of *Chrysanthemum* X *morifolium* 'PPP CONT 09', disclosed in U.S. Plant Pat. No. 21,483. In side-by-side comparisons, plants of the new *Chrysanthemum* differ from plants of 'PPP CONT 09' in the following characteristics:

1. Plants of the new *Chrysanthemum* are more vigorous than plants of 'PPP CONT 09'.
2. Leaves of plants of the new *Chrysanthemum* are smaller and lighter green in color than leaves of plants of 'PPP CONT 09'.
3. Ray florets of plants of the new *Chrysanthemum* are darker red purple in color than ray florets of plants of 'PPP CONT 09'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'GED17VIG8R' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum* X *morifolium* 'GED17VIG8R'.

Parentage: Naturally-occurring whole plant mutation of *Chrysanthemum* X *morifolium* 'Vigorelli Violet', disclosed in U.S. Plant Pat. No. 23,965.

Propagation:

*Type*.—Vegetative terminal cuttings.

*Time to initiate roots, summer*.—About 14 days at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; typically light brown in color, actual color of the roots dependent on substrate composition, water quality, fertilizer, substrate temperature and age of roots.

*Rooting habit*.—Freely branching; medium density.

Plant description:

*Appearance*.—Perennial decorative-type *Chrysanthemum*; stems upright and outwardly spreading giving a uniformly rounded appearance to the plant; plants nearly spherical in overall shape; very freely branching habit, about 25 primary lateral branches develop per plant, each primary lateral branch with multiple secondary branches; pinching is not required, however, will enhance lateral branch development; dense and full plant habit; vigorous growth habit; rapid growth rate.

*Plant height*.—About 50 cm.

*Plant width*.—About 65 cm.

*Lateral branches*.—Length: About 25 cm. Diameter: About 2 mm to 3 mm. Internode length: About 2 cm to 2.5 cm. Strength: Strong, flexible. Aspect: Upright to outwardly spreading. Texture and luster: Fine pubescence; longitudinally ridged; matte. Color: Close to 144A.

*Leaves*.—Arrangement: Alternate, simple. Length: About 5.5 cm to 7 cm. Width: About 3.5 cm to 4 cm. Apex: Rounded to cuspidate. Base: Attenuate. Margin: Palmately lobed and serrate, sinuses between lateral lobes divergent to parallel. Texture and luster, upper and lower surfaces: Slightly pubescent; matte. Color: Developing and fully expanded leaves, upper surface: Close to 136A; venation, close to 148C. Developing and full expanded leaves, lower surface: Close to 137A; venation, close to 147B to 147C. Petioles: Length: About 1 cm. Diameter: About 2 mm. Texture and luster, upper and lower surfaces: Slightly pubescent; slightly rough; matte. Color, upper surface: Close to 146C. Color, lower surface: Close to 146D.

Inflorescence description:

*Appearance*.—Decorative-type inflorescence form; inflorescences borne on terminals above foliar plane; disc and ray florets arranged acropetally on a capitulum.

*Fragrance*.—Faintly fragrant, pungent.

*Flowering time*.—Under natural season conditions, plants flower in early October in Belgium; response time is about 47 days.

*Postproduction longevity*.—Inflorescences maintain good color and substance for about six weeks on the plant grown in an outdoor nursery; inflorescences persistent.

*Quantity of inflorescences*.—Freely flowering habit with about 20 inflorescences developing per lateral branch with numerous inflorescences developing per plant.

*Inflorescence buds*.—Height: About 5 mm. Diameter: About 8 mm. Shape: Globular. Texture and luster: Smooth, glabrous; matte. Color: Close to 59A.

*Inflorescence size and shape*.—Diameter: Relatively large, about 5 cm to 5.5 cm. Depth (height): About 4 cm. Disc diameter: About 1 mm.

*Receptacles*.—Diameter: About 3 mm. Height: About 2.5 mm to 3 mm. Shape: Circular; raised dome. Texture and luster: Smooth, glabrous; matte. Color: Close to 144B.

*Ray florets*.—Quantity and arrangement: More than 200 ray florets per inflorescence arranged in about ten whorls. Length: About 3 cm to 4 cm. Width: About 6 mm. Shape: Oval. Apex: Rounded. Base: Attenuate. Margin: Entire. Aspect: Mostly flat. Texture and luster, upper and lower surfaces: Smooth, glabrous; matte. Color: When opening, upper surface: Close to 59A. When opening, lower surface: Close to 59B. Fully opened, upper surface: Close to 59B; color becoming closer to 181B with development. Fully opened, lower surface: Close to 185B; color becoming closer to 184D with development.

*Disc florets*.—Quantity and arrangement: Less than 20 disc florets per inflorescence and spirally massed at the center of the receptacle; mostly inconspicuous. Length: About 3 mm. Diameter: About 0.5 mm to 1 mm. Shape: Tubular, elongated; apices acute. Texture and luster: Smooth, glabrous; glossy. Color: Apex: Close to 144C. Mid-section: Close to 5B. Base: Close to 145D.

*Phyllaries*.—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin:

Entire; translucent. Texture and luster, upper and lower surfaces: Smooth, glabrous; matte. Color, upper surface: Close to 137A. Color, lower surface: Close to N137B.

*Peduncles*.—Length, terminal peduncle: About 4 cm. Length, fourth peduncle: About 6 cm. Length, seventh peduncle: About 8 cm. Diameter: About 2 mm. Angle, lateral peduncles: About 30° from vertical. Strength: Moderately strong. Texture and luster: Slightly pubescent; matte. Color: Close to 146B.

*Reproductive organs*.—Androecium: None observed. Gynoecium: None observed.

*Seeds and fruits*.—Seed and fruit production have not been observed on plants of the new *Chrysanthemum* to date.

Disease & pest resistance: Resistance to pathogens and pests common to *Chrysanthemum* plants has not been observed on plants of the new *Chrysanthemum* grown under commercial production conditions to date.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'GED17VIG8R' as illustrated and described.

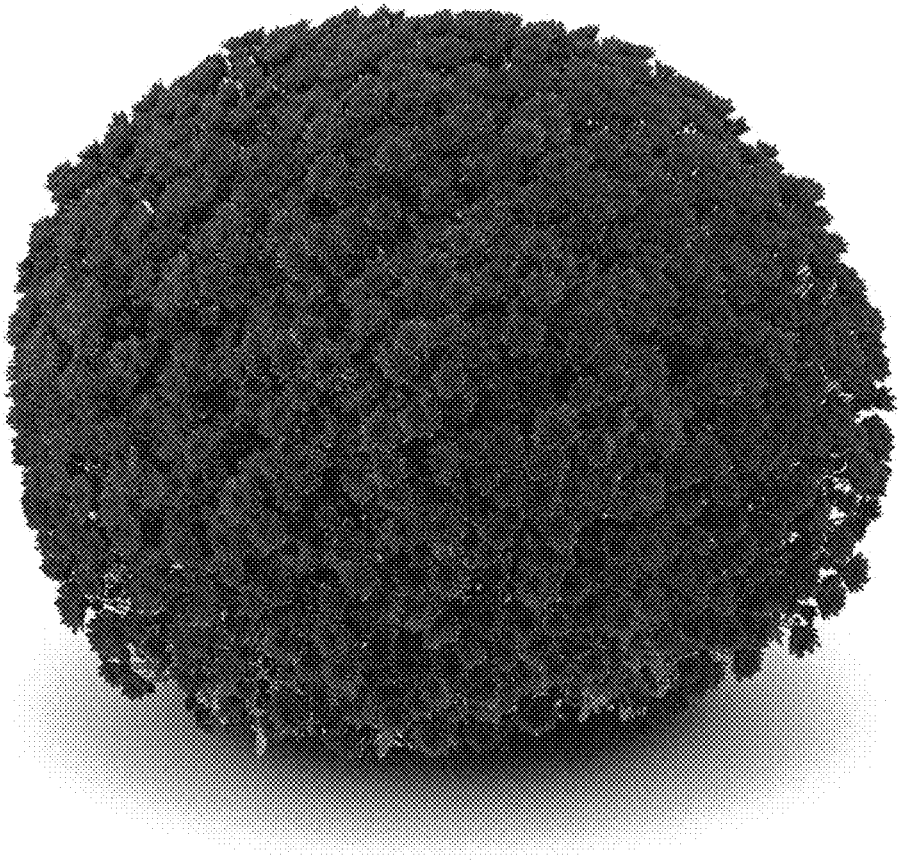

* * * * *